US005288923A

United States Patent [19]

Fennhoff et al.

[11] Patent Number: 5,288,923

[45] Date of Patent: Feb. 22, 1994

[54] PREPARATION OF ETHERS OF DIPHENOLS

[75] Inventors: Gerhard Fennhoff, Willich; Wolfgang Jacob, Moers; Manfred Ehlert, Dormagen, all of Fed. Rep. of Germany

[73] Assignee: Bayer Aktiengesellschaft, Leverkusen, Fed. Rep. of Germany

[21] Appl. No.: 10,726

[22] Filed: Jan. 29, 1993

[30] Foreign Application Priority Data

Jan. 31, 1991 [DE] Fed. Rep. of Germany ....... 4202740

[51] Int. Cl.[5] ..................... C07C 41/01; C07C 315/04

[52] U.S. Cl. ...................................... 568/640; 568/33; 568/638; 568/643; 568/644

[58] Field of Search ................. 568/640, 643, 638, 33, 568/644

[56] References Cited

FOREIGN PATENT DOCUMENTS 2619831 11/1977 Fed. Rep. of Germany .

3529984 3/1987 Fed. Rep. of Germany .

*Primary Examiner*—Marianne M. Cintins

*Assistant Examiner*—Margaret J. Page

*Attorney, Agent, or Firm*—Joseph C. Gil; Aron Preis

[57] ABSTRACT

A process for the preparation of hydroxyalkyl ethers of diphenols is disclosed. Accordingly, aromatic polycarbonate resin is reacted with alkylene diol in the presence of a basic catalyst, at temperatures of 150° to 250° C. at a molar ratio of 514 10 moles of alkylene diol to 1 mole of aromatic carbonate structural units to produce the corresponding hydroxyalkyl ether. Additional embodiments entail optional reactions of the aromatic polycarbonate with cyclic alkylene carbonate and with open chain monomeric bis-(hydroxyalkyl)-carbonate. Aromatic polycarbonate waste may thus be advantageously recycled.

5 Claims, No Drawings

PREPARATION OF ETHERS OF DIPHENOLS

FIELD OF THE INVENTION

The invention relates to a process for the preparation of hydroxyalkyl ethers of diphenols especially to a reaction entailing aromatic polycarbonate resin and alkylene diols.

SUMMARY OF THE INVENTION

A process for the preparation of hydroxyalkyl ethers of diphenols is disclosed. Accordingly, aromatic polycarbonate resin is reacted with alkylene diol in the presence of a basic catalyst, at temperatures of 150° to 250° C. at a molar ratio of 5-10 moles of alkylene diol to 1 mole of aromatic carbonate structural units to produce the corresponding hydroxyalkyl ether. Also disclosed are embodiments of the invention which entail optional additional reactions of the aromatic polycarbonate with cyclic alkylene carbonate and/or with open chain monomeric bis-(hydroxyalkyl)-carbonate. Aromatic polycarbonate waste may be advantageously recycled in accordance with the process of the invention to yield useful products.

BACKGROUND OF THE INVENTION

DE-OS 3 529 984 (LeA 24 047) describes the reaction of 5 diols with polycarbonates to form diphenol carbonates of diols, the diols having a molecular weight Mn of from 300 to 15,000. JA 69-11377 describes the etherification of OH end groups of polyethyleneglycol by a treatment with diphenylcarbonate. DE-OS 2 619 831 (LeA 16 933) describes the preparation of carbonic acid aryl esters of polyalkylene oxide polyols. None of these literature references provides any suggestion for the process according to the invention.

DETAILED DESCRIPTION OF THE INVENTION

The present invention relates to a process for the preparation of hydroxyalkyl ethers of diphenols, characterized in that aromatic polycarbonates based on diphenols are reacted with alkylene diols and optionally also with cyclic alkylene carbonates or optionally also with open chain monomeric bis-(hydroxyalkyl)-carbonates at temperatures of from 150° to 250° C., preferably from 170° to 220° C., optionally in the presence of basic catalysts, in which a) for the reaction with alkylene diols, the quantitative proportions are from 5 to 10 mol of alkylene diols, based on 1 mol of aromatic carbonate structural units, b) when an additional reaction is carried out with cyclic alkylene carbonates, the quantitative proportions are from 1 to 1.5 mol of alkylene carbonate, based on 1 mol of aromatic carbonate structural units, and c) when an additional reaction is carried out with open chain monomeric bis-(hydroxyalkyl)-carbonates, the quantitative ratios are from 1 to 1.5 mol of monomeric bis-(hydroxyalkyl)-carbonate, based on I mol of aromatic carbonate structural units.

Aromatic polycarbonates based on diphenols in the sense of the present invention are the known thermoplastic materials such as are available commercially and well known from the literature (see, for example, "H. Schnell, Chemistry and Physics of Polycarbonates, Interscience Publishers, New York 1964", U.S. Pat. No. 3,028,365 and DE-OS 3 832 396). Among the suitable polycarbonates are the commercial resins which are available from Bayer AG under the Makrolon trademark.

These suitable polycarbonates may be based on any diphenols. The following are examples of these: Hydroquinone, resorcinol, dihydroxydiphenyls, bis-(hydroxyphenyl)-alkanes, bis-(hydroxyphenyl)-cycloalkanes,bis-(hydroxyphenyl)-sulphides, bis-(hydroxphenyl)-ethers, bis-(hydroxyphenyl)-ketones, bis-(hydroxyphenyl)-sulphones,bis-(hydroxyphenyl)-sulphoxides and $\alpha,\alpha'$-bis-(hydroxyphenyl)-diisopropylbenzenes, and derivatives thereof which are alkylated and/or halogenated in the nucleus.

The following are preferred diphenols on which the suitable aromatic polycarbonates may be based: 4 4'-dihydroxydiphenyl, 2,2-bis-(4-hydroxyphenyl)-propane, 2,4-bis-(4-hydroxyphenyl)-2-methylbutane, 1,1-bis-(4-hydroxyphenyl)-p-diisopropylbenzene, 2,2-bis-(3-methyl-4hydroxyphenyl)-propane, 2,2-bis-(3-chloro-4-hydroxyphenyl)-propane, bis-(3, 5-dimethyl-4-hydroxyphenyl)-methane, 2,2-bis-(3,5-dimethyl-4-hydroxyphenyl)-propane, bis-(3,5-dimethyl-4-hydroxyphenyl)-sulphone, 2,4-bis-(3,5-dimethyl-4-hydroxyphenyl)-2-methylbutane, 1,1-bis-(3,5-dimethyl-4-hydroxyphenyl)-p-diisopropylbenzene, 2, 2-bis-(3,5-dichloro-4-hydroxyphenyl)-propane, 2,2-bis-(3,5-dibromo-4-hydroxyphenyl)-propane and 1,1-bis-(4-hydroxyphenyl)-3,3,5-trimethylcyclohexane.

The molecular weights Mw (weight average determined by known methods, for example by measuring the $Y_{rel}$ in $CH_2Cl_2$ at 25° C. and at a concentration of 0.5 g in 100 ml of $CH_2Cl_2$) of the polycarbonates are from 5000 to 200,000, preferably from 10,000 to 100,000 and especially from 15,000 to 80,000.

The polycarbonates may be straight chain or branched and may be homopolycarbonates or copolycarbonates, randomly structured copolycarbonates or block copolycarbonates.

Alkylene diols for the purpose of the present invention may be, for example, those of $C_2$–$C_{22}$-alkylenes, preferably $C_2$–$C_9$-alkylenes, in which the two alcoholic OH groups are not arranged geminally. The alkylene groups may be straight chain or branched; 1,2-diols, 1,3-diols, 1,4-diols and 1,6-diols are preferred diols.

Cyclic alkylene carbonates are those of the above mentioned 1,2-diols and 1,3-diols of the above-mentioned $C_2$–$C_{22}$-alkylene diols.

Open chain monomeric bis-(hydroxyalkyl)-carbonates are, for example, those of the above-mentioned $C_2$–$C_{22}$- alkylene diols.

Examples of suitable basic catalysts include alkali metal hydroxides, alkaline earth metal hydroxides, aqueous $NH_3$ solutions and amines. Alkali metal hydroxides are preferred, in particular NAOH and KOH. The quantity by weight of basic catalyst is from 10 ppm to 1000 ppm, based on the weight of the polycarbonate put into the process. The reaction according to the invention is preferably carried out under inert gas.

The reaction according to the invention yields pure bis-hydroxy-alkyl ethers of the diphenols on which the polycarbonates are based or mixtures of these bis-ethers and the corresponding monoethers of the diphenols on which the polycarbonates are based and the diphenols themselves, depending on the selected reaction conditions and the reactants. The particular reaction conditions employed can easily be determined by those skilled in the art.

The process variations b) and c) according to the invention only give rise to the corresponding bis-ethers in the pure form.

Bis-ethers of the diphenols are known from the literature (see, for example, J. Am. Chem. Soc., Volume 79 (1956), page 674). Monoethers of the diphenols are also known from the literature. Mixtures of bisethers, monoethers and diphenols obtainable according to the invention are new.

The present invention thus also relates to mixtures of bis-ethers of diphenols, monoethers of diphenols and diphenols themselves, obtainable by the process according to the invention.

The bis-ethers may be isolated from the mixtures by crystallization. The monoethers may also be isolated from the mixtures by crystallization and the diphenols may also be isolated from the mixtures by crystallization.

When copolycarbonates are used, the corresponding mixtures of the diphenols on which these copolycarbonates are based or mixtures of monoethers or mixtures of bisethers are obtained.

The corresponding individual compounds may in principle also be isolated from such mixtures.

The bisethers of diphenols, monoethers of diphenols and diphenols themselves obtainable by the process according to the invention may be re-used as such in known manner for syntheses in organic chemistry.

The mixtures of bisethers, monoethers and diphenols obtainable by the process according to the invention may also be used for syntheses in organic chemistry, for example for the production of lacquers or epoxy resins.

The main advantage of the process according to the invention, however, lies in the fact that all sorts of polycarbonate wastes can be used as the aromatic polycarbonate reactant.

The present invention thus also relates to a process where the aromatic polycarbonate based on diphenols is polycarbonate waste.

The process according to the invention thus enables inferior waste products which would otherwise have to be disposed of to be used for the production of high quality chemicals and lacquer raw materials.

Further advantages of the process according to the invention lie in the substantial reduction in reaction times by one to five hours and the elimination of expensive purification processes such as the adsorption of impurities on active charcoal.

The invention is further illustrated but is not intended to be limited by the following examples in which all parts and percentages are by weight unless otherwise specified.

EXAMPLES

Bisphenol-A-homopolycarbonate having a relative solution viscosity of 1.279 (determined in methylene chloride at 25° C., 0.500 g of polycarbonate in 100 ml of methylene chloride) was used for all the experiments described below.

Example 1 Synthesis of 2,2bis-(4-β-hydroxyethoxyphenyl)-propane 0.200 g of Sodium hydroxide powder are dissolved in 360 g of ethylene glycol (5.8 mol) and 200 g of polycarbonate (0.8 mol) are added thereto. The mixture is heated to 180° C. with constant stirring and introduction of nitrogen so that mild reflux takes place. After 2 hours, when all the polycarbonate has dissolved, 69.3 g of ethylene carbonate (0.8 mol) are added. The temperature is maintained at 180° C. for a further 2 hours while nitrogen is passed through and the reaction mixture is then left to cool to room temperature.

The white precipitate obtained when the solution is cold is filtered off and recrystallized from ethyl acetate.

Yield: 162.7 g

Melting point: 112° C.

Example 2 Synthesis of 2,2-bis-(4-Y-hydroxypropyl oxyphenyl)-propane 0.200 g of Sodium hydroxide powder are dissolved in 500 g of propylene glycol (6.5 mol) and 200 g of polycarbonate (0.8 mol) are added thereto. The mixture is heated to 180° C. with constant stirring and introduction of nitrogen so that mild reflux occurs. After 2 hours, when all the polycarbonate has dissolved, 80.3 g of 1,3-propylene carbonate (0.8 mol) are added. The temperature is maintained at 180° C. for a further 2 hours while nitrogen is passed through and the reaction mixture is then left to cool to room temperature.

The white precipitate formed when the solution is cold is filtered off, washed several times with cold water and dried in a vacuum drying cupboard.

Yield: 159 g

Melting point 61° to 63° C.

What is claimed is:

1. A process for the preparation of hydroxyalkyl ethers of diphenols comprising reacting
   (i) an aromatic polycarbonate resin which is based on at least one diphenol and having a weight average molecular weight of about 5000 to 200,000, with
   (ii) at least one alkylene diol, in the presence of a basic catalyst at temperatures of 150° to 250° C., at a molar ratio of about 5–10 moles of said diol to 1 mole of aromatic carbonate structural units.

2. The process of claim 1 wherein said reaction further comprises reacting (iii) a cyclic alkylene carbonate at a molar ratio of about 1–1.5 moles of said cyclic alkylene carbonate to 1 mole of aromatic carbonate structural units.

3. The process of claim 1 wherein said reaction further comprises reacting (iv) an open chain monomeric bis-(hydroxyalkyl)-carbonate at a molar ratio of about 1–1.5 moles of said open chain monomeric bis(hydroxyalkyl)-carbonate to 1 mole of aromatic carbonate structural units.

4. The process of claim 1 wherein said alkylene diol is a $C_{2-22}$ alkylene diol.

5. The process of claim 1 wherein said polycarbonate is a waste resin.

* * * * *